United States Patent [19]

Kussmaul et al.

[11] Patent Number: 4,564,682

[45] Date of Patent: Jan. 14, 1986

[54] PROCESS FOR THE PREPARATION OF HETEROCYCLIC PHENYL ETHERS

[75] Inventors: Ulrich Kussmaul, Karben; Johannes Becherer, Maintal; Reinhard Handte, Hofheim; Rolf Müller, Karben, all of Fed. Rep. of Germany

[73] Assignee: Cassella Aktiengesellschaft, Frankfurt Am Main, Fed. Rep. of Germany

[21] Appl. No.: 583,713

[22] Filed: Feb. 27, 1984

[30] Foreign Application Priority Data

Mar. 28, 1983 [DE] Fed. Rep. of Germany ....... 3311285

[51] Int. Cl.$^4$ .......................................... C07D 277/68
[52] U.S. Cl. ................................... 548/169; 548/165; 548/221; 548/329; 71/88; 71/90; 71/92
[58] Field of Search .............. 548/165, 178, 169, 221, 548/329

[56] References Cited

U.S. PATENT DOCUMENTS

| | | | |
|---|---|---|---|
| 3,849,431 | 11/1974 | Gallay et al. | 548/165 |
| 3,933,841 | 1/1976 | Brenneisen et al. | 548/329 |
| 4,130,413 | 12/1978 | Handte et al. | 548/329 |
| 4,263,440 | 4/1981 | Handte | 548/165 |

Primary Examiner—John Kight
Assistant Examiner—Garnette D. Draper
Attorney, Agent, or Firm—Connolly and Hutz

[57] ABSTRACT

A compound of the formula

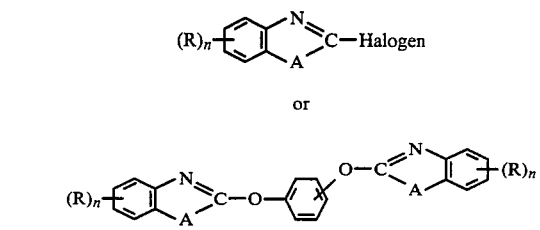

or

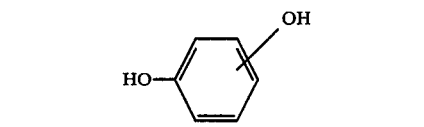

is reacted with a phenol of the formula

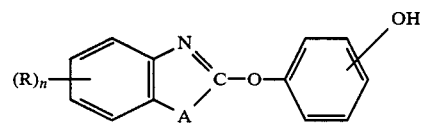

in the presence of an acid to produce a heterocyclic phenyl ether of the formula wherein each R is independently selected from halogen, trifluoromethyl, nitro, cyano, alkyl having 1 to 4 carbon atoms, alkoxy having 1 to 4 carbon atoms or alkylthio having 1 to 4 carbon atoms;
A is oxygen, sulfur or N-alkyl having 1 to 4 carbon atoms; and
n is a number from 0 to 3.

7 Claims, No Drawings

PROCESS FOR THE PREPARATION OF HETEROCYCLIC PHENYL ETHERS

The present invention relates to a process for the preparation of heterocyclic phenyl ethers of the formula I

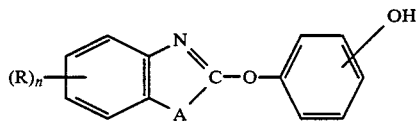

in which R denotes identical or different radicals from the group comprising halogen, $CF_3$, $NO_2$, CN, $(C_1-C_4)$alkyl, $(C_1-C_4)$-alkoxy or $(C_1-C_4)$alkylthio, A denotes O, S or N-$(C_1-C_4)$alkyl, and n denotes 0 to 3, which entails reacting a compound of the formula II

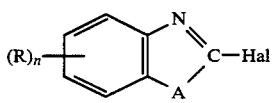

in which Hal represents halogen, preferably Cl or Br, or a compound of the formula IV

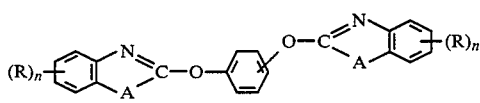

with a compound of the formula III

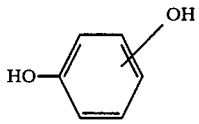

A process of this type has already been disclosed in European Patent Specification 924. In this known process, the reaction is carried out, according to the conditions, in the presence of basic compounds. The bases are employed in this reaction in at least stoichiometric amounts or exceeding them by 10 to 20% (compare European Patent Specification 924, page 3, lines 34 to 35). This known process provides the heterocyclic phenyl ethers of the formula I in good yields, but it has some disadvantages. Thus, after completion of the reaction, it is necessary to remove the salt which is formed. Since solvent still adheres to the salt which has been removed, it is not possible to dispose of it directly in the form as removed. Furthermore, in order to obtain the desired compounds I, it is necessary to acidify the reaction mixture remaining after removal of the salt, this requiring use of additional acid and increasing the salt load of the process. For both economic and ecological reasons, it is necessary to recover the solvents used in the known process. Since the reaction mixtures undergo aqueous work-up, the recovery of solvents which are miscible with water, for example the polar aprotic solvents which are preferably used, is generally only possible by costly distillation.

It has now been found, surprisingly, that the disadvantages of the known process can be avoided by carrying out the reaction in the presence of an acid and, preferably, without a solvent.

Using the process according to the invention, compounds of the formula II or compounds of the formula IV or mixtures of compounds of the formulae II and IV can be reacted with compounds of the formula III.

The acids used are Lewis acids or strong non-oxidising mineral acids or organic acids. Examples of suitable mineral acids are phosphoric acid or hydrogen halides, especially hydrogen chloride. Examples of suitable organic acids are trifluoroacetic acid or p-toluene phosphonic acid. The acid employed in amounts which range from catalytic to equimolar, based on the starting compounds II or IV. Volatile acids, such as hydrogen halides, especially hydrogen chloride, are preferred, since they can readily be removed from the reaction mixture after reaction is complete by raising the temperature and/or blowing out with an inert gas, such as, for example, nitrogen. During the reaction, gaseous acids are passed in a gentle stream through the reaction mixture.

When compounds II are used alone or mixed with compounds IV as the starting products, then the addition of an acid is generally unnecessary, since the hydrogen halide which is formed from compound II during the reaction is sufficient for carrying out the reaction. Of course, carrying out the process according to the invention without special addition of acid is preferred.

The process according to the invention is carried out in a suitable solvent or solvent mixture or, preferably, without a solvent. The solvents which are used must be inert to the reactants. Aromatic hydrocarbons and halogenated hydrocarbons which are insoluble in water, such as, for example, toluene, o-, m- and p-xylene, particularly in the form of the technical mixture of xylenes, and chlorobenzene, are particularly suitable. However, it is also possible to use polar aprotic solvents, for example acid amides, such as dimethylformamide, dimethylacetamide, diethylacetamide, N-methylpyrrolidone and hexamethylphosphoric triamide, also dimethyl sulphoxide or nitriles, such as acetonitrile or propionitrile, as the solvent.

The reaction temperatures are between 50° and 300° C., preferably at 100° to 200° C. and, when the process is carried out without a solvent, are preferably above the melting point of the compound III. At reaction temperatures above the boiling point of the solvent used, the reaction is carried out in a closed vessel. When using starting compounds of the formula II alone or mixed with starting compounds of the formula IV, the process is preferably carried out without the addition of an acid. In this case, it is frequently advantageous to carry out the reaction at relatively low temperature, in order to prevent the hydrogen halide which is formed during the reaction from escaping too rapidly from the reaction mixture. The hydrogen halides escaping from the reaction mixture during the reaction can be absorbed, for example in water or dilute solution of alkali, in a known manner using standard equipment, and used for other purposes.

The molar ratios of the reactants II: III and IV:III and (II+IV):III can be varied within wide limits. It is possible to employ equimolar amounts. An excess of compounds III of at least 5 mol-% is advantageous. However, it is also possible to employ a twice molar to 5-molar excess of compounds of the formula III. Hence, the molar ratios of the reactants II:III and IV:III and (II+IV):III are normally 1:(1.05 to 5), preferably 1:(1.05 to 2). There is no advantage in using a greater than 5-molar excess of compound III.

In general, the process according to the invention is carried out in such a manner that the dihydroxybenzene III is introduced first, optionally in a solvent and optionally with an acid, and heated to the reaction temperature, and the compound II or IV or a mixture of the compounds II and IV is appropriately added with stirring. As already mentioned, when using compounds II, the addition of an acid is unnecessary since vigorous evolution of hydrogen halide starts a short time after the reaction temperature is reached when the compound II has been added. The hydrogen halide escaping from the reaction mixture, whether it is the excess of hydrogen halide which has been passed in or the hydrogen halide which is liberated during the reaction, is absorbed in a known manner. However, the sequence of addition of the reactants is of subordinate importance; it is also possible to add the reactants at the same time, or the reactants of the formula II or IV can be introduced first. However, it is preferable to introduce the compounds III first. In all cases, the reaction times are short, being 10 minutes to 12 hours. Surprisingly, in all cases they are markedly shorter than for the known process according to European Pat. No. 924. The progress of the reaction can readily be followed by thin-layer chromatography. The process according to the invention is generally carried out under a protective gas, such as, for example, a noble gas, carbon dioxide or nitrogen. The use of nitrogen as the protective gas is preferred. When using a volatile acid, after reaction is complete, it is removed from the reaction mixture by raising the temperature and/or blowing out with protective gas. When using a solvent, the mixture is cooled and worked up in a suitable manner. Normally, the residue is filtered off with suction and introduced into water, care being taken during this that a pH of 7 is maintained by addition of a solution of alkali (such as, for example, sodium hydroxide or potassium hydroxide solution) or a buffer (such as, for example, disodium hydrogen phosphate). The suspension is then heated, normally to boiling, and filtered hot. The mixtures obtained without using a solvent are introduced into water, a pH of 7 again being maintained by the addition of a solution of alkali or of buffers. Again, the suspension is heated, normally to boiling, and filtered hot.

The heating in water brings about dissolution of excess dihydroxybenzenes III which can be recovered from the filtrate in a simple and known manner, for example by cooling and allowing to crystallise, where appropriate after previous concentration.

Generally, for further processing, it is unnecessary to purify further the compounds I which are obtained. If desired, further purification can be carried out by known methods, such as recrystallisation, distillation or reprecipitation.

In some cases, depending on the molar ratio of the starting products III and II, the final products I which are obtained contain by-products of the formula IV. In cases of interference by this content of compounds IV, these by-products can readily be removed because they are sparingly soluble in water and organic solvents, and they can be employed in subsequent batches as the starting product, possibly together with starting product II, and reacted to give compounds I.

Other processes for carrying out and working up the reactions are described in the examples.

In every case, the quality of the products obtained using the process according to the invention reaches the state of the art or even exceeds this in some cases.

The process according to the invention is preferably used for the preparation of those compounds of the formula I in which R denotes identical or different radicals from the group comprising halogen, especially fluorine, chlorine and bromine, $CF_3$, $NO_2$ and methyl, and is also preferred for the preparation of compounds I in which n denotes 0, 1 or 2. In the case where A in formula I represents N-($C_1$-$C_4$)alkyl, A preferably denotes N—$CH_3$.

The compounds of the formula I are valuable precursors of effective biocides, for example for herbicides, especially for those proposed in U.S. Pat. No. 4,130,413. According to this patent, valuable selective herbicides are obtained from the compounds of the formula I, for example by reaction with 2-halogenopropionic acid derivatives, such as esters and amides, in a manner known per se. For example, ethyl 2-(4'-(6''-chloro-2''-benzothiazolyloxy)phenoxy)propionate is produced from 4-(6'-chloro-2'-benzothiazolyloxy)phenol and ethyl 2-bromopropionate in the presence of potassium carbonate.

The starting compounds of the formula II can be prepared by known processes, for example from the corresponding 2-mercapto or 2-oxo compounds by halogenation, or from the 2-amino compounds by diazotisation followed by a Sandmeyer reaction (see, for example, C. A. 59,396 j; Am Chem. J. 21 (1899), 111).

The 2-halogeno compounds of appropriately substituted benzothiazoles, benzoxazoles and 1-alkylbenzimidazoles can be used as starting compounds of the formula II. Examples of these are the following: 2-chloro-benzoxazole, -1-methylbenzimidazole; 2-chloro-6-fluorobenzothiazole, -benzoxazole, -1-methylbenzimidazole; 2,6-dichlorobenzothiazole, -benzoxazole, -1-butylbenzimidazole; 2,5-dichlorobenzothiazole, -benzoxazole, -1-methylbenzimidazole; 2-chloro-5-methyl-benzothiazole, -benzoxazole, -1-methylbenzimidazole; 2-chloro-6-methyl-benzothiazole, -benzoxazole, -1-methylbenzimidazole; 2-chloro-6-ethyl-benzothiazole, -benzoxazole, -1-methylbenzimidazole; 2-chloro-6-nitro-benzothiazole, -benzoxazole, -1-methylbenzimidazole; 2,5-dichloro-6-nitro-benzothiazole, -benzoxazole, -1-methylbenzimidazole; 2-chloro-5-methoxy-benzothiazole, -benzoxazole, -1-methylbenzimidazole; 2-chloro-6-methoxy-benzothiazole, -benzoxazole, -1-methylbenzimidazole; 2-chloro-6-methylthio-benzothiazole, -benzoxazole, -1-methylbenzimidazole; 2,5,6-trichloro-benzothiazole, -benzoxazole, -1-methylbenzimidazole; 2-chloro-5-bromo-benzothiazole, -benzoxazole, -1-methylbenzimidazole; 2-chloro-6-bromo-benzothiazole, -benzoxazole, -1-methylbenzimidazole; 2-chloro-5,6-dibromo-benzothiazole, -benzoxazole, -1-methylbenzimidazole; 2-chloro-5-trifluoromethyl-benzothiazole, -benzoxazole, -1-methylbenzimidazole; 2-chloro-6-trifluoromethylbenzothiazole, -benzoxazole, -1-methylbenzimidazole; 2-chloro-6-cyano-benzothiazole, -benzoxazole, -1-methylbenzimidazole, and the corresponding 2-bromo derivatives.

The starting compounds III, catechol, resorcinol and hydroquinone, are known. The use of hydroquinone is preferred.

The starting compounds of the formula IV are produced as by-products which are in themselves undesired during the reaction of compounds II with compounds III, especially when the compounds II are present in excess in the reaction.

The fact that, using the process according to the invention, unsymmetrical ethers can be prepared in a simple and smooth reaction from hydroxyl and halogen compounds without the presence of bases has to be denoted extremely surprising, since the addition of a base or the use of an alcoholate or phenolate has hitherto always applied to the so-called Williamson's ether synthesis, compare C. Ferri: Reaktionen der organischen Synthese (Reactions in organic synthesis) (1978), page 396.

Carrying out the process according to the invention without a solvent gives rise to a high space yield and, on the other hand, saves the cost of regenerating the solvent.

The process according to the invention is illustrated further, but is not restricted, by the examples which follow.

EXAMPLE 1

4-(6'-Chloro-2'-benzothiazolyloxy)phenol

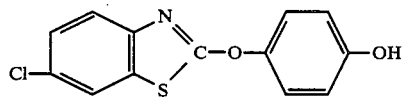

220.0 g (2 mol) of hydroquinone are fused under a protective atmosphere of $N_2$ gas in a reaction vessel having a stirrer and a gas outlet tube. 204.1 g (1 mol) of molten 2,6-dichlorobenzothiazole are run in, with stirring, over the course of 25 minutes at an internal temperature of 175° C. Vigorous evolution of hydrogen chloride starts. (The exit gas is absorbed in water in a customary manner to give aqueous hydrochloric acid.) After addition of the 2,6-dichlorobenzothiazole is complete, the mixture is stirred at 168° to 170° C. for 1 h. A check by thin-layer chromatography then shows that reaction is complete.

To work up, the mixture is immediately introduced in a finely divided form while still hot into 1.5 liters of vigorously stirred water, the mixture is neutralised with a little sodium hydroxide solution and boiled at 100° C. for 10 minutes. It is filtered hot and the solid is washed with a little hot water. After drying at 70° C. under a pressure of about 20 mbar, 273.5 g (98.5% of theory) of 4-(6'-chloro-2'-benzothiazolyloxy)phenol of melting point 174° to 177° C. are obtained. Recrystallisation from toluene provides a product of melting point 178° to 179° C.

Excess hydroquinone precipitates out after concentrating and cooling the aqueous filtrate which is obtained. It is filtered off and, after drying, used for a new batch.

EXAMPLE 2

4-(6'-Chloro-2'-benzoxazolyloxy)phenol

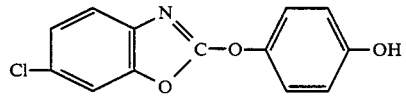

200 ml of xylene, 37.6 g (200 mmol) of 2,6-dichlorobenzoxazole and 44.0 g (400 mmol) of hydroquinone in a four-neck flask having a stirrer, reflux condenser, internal thermometer and gas introduction tube are, after flushing the apparatus with nitrogen, heated, with stirring, to an internal temperature of 120° C. The escaping hydrogen chloride gas is absorbed as in Example 1. After 4 h, the mixture is briefly heated to reflux and nitrogen is passed over to drive out the dissolved hydrogen chloride. The mixture is cooled to room temperature and filtered with suction.

The paste which is moist with xylene is vigorously stirred with 100 ml of water, the pH is adjusted to 7 with about 1 to 1.5 g of $Na_2HPO_4$, and the xylene is removed by steam distillation. The mixture is filtered hot with suction, and the solid is washed with about 150 ml of hot water. After drying at 70° C. under about 20 mbar, 46.3 g (88% of theory) of 4-(6'-chloro-2'-benzoxazolyloxy)phenol of melting point 181°–183° C. are obtained.

Excess hydroquinone crystallises out of the filtrate on cooling.

When, in a repetition of the example, the reaction temperature is increased to 135° to 140° C., the reaction time increases to about 8 h. When, in a repetition of the example, the reaction is carried out by boiling under reflux, it is no longer possible to carry out the reaction reasonably without adding additional acid, since the hydrogen chloride being formed from the 2,6-dichlorobenzoxazole escapes too rapidly from the reaction mixture at the reflux temperature of xylene (about 144° C.).

EXAMPLE 3

4-(6'-Chloro-2'-benzothiazolyloxy)phenol 60.5 g (0.55 mol) of hydroquinone and 102.0 g (0.5 mol) of 2,6-dichlorobenzothiazole are reacted in analogy to Example 1. The reaction mixture after reaction is directly recrystallised from methanol. 124.1 g of 4-(6'-chloro-2'-benzothiazolyloxy)-phenol (89.4% of theory) are obtained, together with, as byproduct, a small amount of hydroquinone 1,4-bis-6'-chloro-2'-benzothiazolyl ether which is insoluble in methanol.

EXAMPLE 4

4-(6'-Chloro-2'-benzothiazolyloxy)phenol 8.3 g (75 mmol) of hydroquinone and 11.1 g (25 mmol) of hydroquinone 1,4-bis-6'-chloro-2'-benzothiazolyl ether and 1 g (5 mmol) of 2,6-dichlorobenzothiazole are heated at 175° to 180° C. for 4 h. Working up in analogy to Example 1 provides 8.0 g (96% of theory) of 4-(6'-chloro-2'-benzothiazolyloxy)phenol.

EXAMPLE 5

4-(6'-Chloro-2'-benzoxazolyloxy)phenol 1.4 liters of xylene, 413 g (1 mol) of 1,4-bis(6'-chloro-2'-benzoxazolyloxy)benzene and 330 g (3 mol) of hydroquinone in a 2 liter four-neck flask having a stirrer, reflux condenser, internal thermometer and gas introduction tube are heated at 120° C., while passing in a gentle stream of HCl gas, and are stirred at this temperature for 3 h. The mixture is then briefly heated to reflux and a little nitrogen is passed through to drive out the HCl gas.

The mixture is cooled to room temperature and filtered with suction. The paste which is moist with xylene is stirred with 1 liter of water, the pH is adjusted to 7 with about 10 to 15 g of $Na_2HPO_4$, and then the xylene is removed by steam distillation. The mixture is filtered hot with suction and washed with 1.5 liters of hot water. After drying, there remain 475 g of 4-(6'-chloro-2'-benzoxazolyloxy)phenol, 95% pure, melting point 175° to 180° C., corresponding to 450 g of 100% pure, which is 86% of theory. The content of bisether is about 4 to 5%, and the content of hydroquinone is about 0.5%. Hydroquinone crystallises out of the filtrate on cooling.

EXAMPLE 6

4-(6'-Chloro-2'-benzoxazolyloxy)phenol 1.4 liters of xylene, 228 g (1.2 mol) of 2,6-dichlorobenzoxazole, 99% pure, 165 g (0.4 mol) of 1,4-bis(6'-chloro-2'-benzoxazolyloxy)benzene and 396 g (3.6 mol) of hydroquinone in a 2 liter four-neck flask having a stirrer, reflux condenser, internal thermometer and gas introduction tube, are, after flushing the apparatus with nitrogen, heated to an internal temperature of 120° to 125° C. About 1.1 mol of hydrogen chloride gas escapes over the course of 3 h. After the evolution of gas has ended, the mixture is stirred at 120° to 125° C. for a further hour, then briefly heated to reflux and nitrogen is passed over to drive out dissolved hydrogen chloride. The mixture is cooled to room temperature and filtered with suction.

The paste which is moist with xylene is stirred into 1 liter of water, the pH is adjusted to 7 with about 10 to 15 g of Na2HPO4, and the xylene is removed by steam distillation. The mixture is filtered hot and the solid is washed with 1.5 liters of hot water. After drying, there remain about 475 g of 4-(6'-chloro-2'-benzoxazolyloxy)phenol, 95% pure, melting point 175° to 180° C., corresponding to about 450 g of 100% pure, which is 86% of theory. Hydroquinone crystallises out of the filtrate on cooling.

In addition, the following are obtained according to Examples 1 to 5:

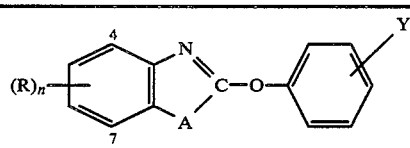

| Example No. | (R)n | A | Y |
|---|---|---|---|
| 7 | 5-CH3 | S | 4-OH |
| 8 | 6-CH3 | S | 4-OH |
| 9 | 6-NO2 | S | 3-OH |
| 10 | 5-Br | S | 4-OH |
| 11 | H | N—CH3 | 4-OH |
| 12 | H | O | 4-OH |
| 13 | H | N—CH3 | 3-OH |
| 14 | 5-Cl | O | 4-OH |
| 15 | 6-Cl | O | 4-OH |
| 16 | H | N—CH3 | 2-OH |
| 17 | 5-Cl 6-CH3 | S | 4-OH |
| 18 | 5,6-di-CH3 | S | 4-OH |
| 19 | 6-C2H5O | S | 4-OH |
| 20 | 7-Cl | S | 4-OH |

What is claimed is:

1. The process for preparation of heterocyclic phenyl ethers of the formula

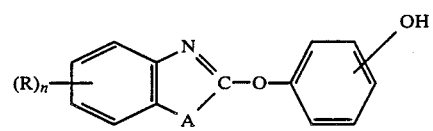

wherein each R is independently selected from halogen, trifluoromethyl, nitro, cyano, alkyl having 1 to 4 carbon atoms, alkoxy having 1 to 4 carbon atoms or alkylthio having 1 to 4 carbon atoms;

A is oxygen, sulfur or N-alkyl having 1 to 4 carbon atoms; and n is a number from 0 to 3;

which process comprises reacting a compound of the formula

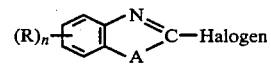

or

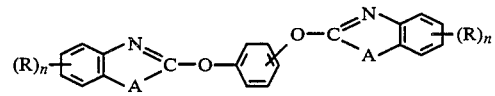

with a compound of the formula

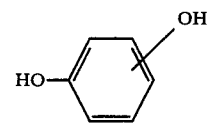

in the presence of an acid.

2. The process according to claim 1 wherein the reactants are reacted at temperatures from 50° to 300° C.

3. The process according to claim 2 wherein the reactants are reacted at temperatures from 100° to 200° C.

4. The process according to claim 1 wherein the acid is hydrogen chloride.

5. The process according to claim 1 wherein the reactants are reacted without additional solvent.

6. The process according to claim 1 wherein the reactants are reacted with

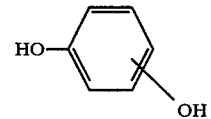

also serving as solvent.

7. The process according to claim 1 wherein

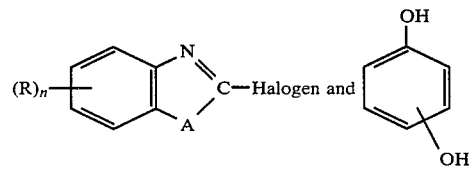

are reacted and the acid is by-product hydrogen halide.

* * * * *

UNITED STATES PATENT AND TRADEMARK OFFICE
CERTIFICATE OF CORRECTION

PATENT NO. : 4,564,682
DATED : January 14, 1986
INVENTOR(S) : Kussmaul et al

It is certified that error appears in the above-identified patent and that said Letters Patent is hereby corrected as shown below:

Column 2, lines 11-12 change "p-toluene phosphonic acid" to read -- p-toluene sulfonic acid --.

Column 5, line 10, insert --been-- before "applied".

Signed and Sealed this

Twenty-fourth Day of June 1986

[SEAL]

Attest:

DONALD J. QUIGG

Attesting Officer

Commissioner of Patents and Trademarks